United States Patent [19]

Kozikowski et al.

[11] Patent Number: 5,547,960

[45] Date of Patent: Aug. 20, 1996

[54] C-10 ANALOGS OF HUPERZINE A

[75] Inventors: Alan P. Kozikowski, Princeton;
Werner Tückmantel, North Brunswick,
both of N.J.

[73] Assignee: Mayo Foundation for Medical Education and Research, Rochester, Mich.

[21] Appl. No.: 302,357

[22] Filed: Sep. 7, 1994

[51] Int. Cl.$^6$ .................. A61K 31/44; C07D 221/06; C07D 221/22
[52] U.S. Cl. .............................................. 514/295; 546/79
[58] Field of Search ............................... 546/79; 514/295

[56] References Cited

U.S. PATENT DOCUMENTS

| | | | |
|---|---|---|---|
| 4,929,731 | 5/1990 | Kozikowski et al. | 546/97 |
| 5,104,880 | 4/1992 | Kozikowski | 514/298 |
| 5,106,979 | 4/1992 | Kozikowski et al. | 546/93 |
| 5,177,082 | 1/1993 | Yu et al. | 514/286 |

OTHER PUBLICATIONS

Y. Ashani et al., "Role of Tyrosine 337 in the Binding of Huperzine A to the Active Site of Human Acetylcholinesterase", *Molecular Pharmacology*, 45, 555–560 (Mar. 1994).

J. R. Atack et al., "Comparative Inhibitory Effects of Various Physostigmine Analogs against Acetyl- and Butyrylcholinesterases", *J. Pharmacol. Exp. Ther.*, 249, 194–202 (1989).

W. A. Ayer et al., "Some new Lycopodium alkaloids", *Can. J. Chem.*, 67, 1077–1086 (Jun. 1989).

W. A. Ayer et al. "Alkaloids of *Lycopodium selago*. On the identity of sealgine with hupertine A and the structure of a related alkaloid", *Can. J. Chem.*, 67, 1538–1540 (Oct. 1989).

S. Chen et al., "The effect of fordine on learning and memory in rats", *Chem. Abs.*, 108, Abstract No. 143270x (1988).

Y. S. Cheng, "128 cases of myasthenia gravis treated with huperzine A", *New Drugs and Clinical Remedies*, 5, 197–199 (1986)–English Language Abstracts included on last page.

D. Gravel et al., "Novel Palladium Catalyzed Bicycloannulation of Monoactivated Cyclic Ketones Using a 1, 3-Allylic Diacetate and an Enolysing Catalyst", *Tetrahedron Letters*, 33, 1407–1410 (1992).

A. P. Kozikowski, "Synthetic Chemistry, Neurotransmission and Second Messengers", *J. Heterocyclic Chem.*, 27, 97–105 (Jan. 1990).

J. Liu et al., "Chemistry of huperzine A and B", *Chem. Abs.*, 1 107, Abstract No. 115821p (1987).

J. S. Liu et al., "The structures of huperzine A and B, two new alkaloids exhibiting marked anticholinesterase activity", *Can. J. Chem.*, 64, 837–839 (Apr. 1986).

X. Tang et al., "Effects of huperzine A on learning and retrieval process of discrimination performance in rats", *Chem. Abs.*, Abstract No. 12878n (1987).

X.-C. Tang et al., "Effects of huperzine A on learning and retrieval process of discrimination performance in rats", *Acta Pharmacol. Sinica*, 7, 507–511 (Nov. 1986)–English Language Abstract included on last page.

X.-C. Tang et al., "Effects of Huperzine A, a New Cholinesterase Inhibitor, on the Central Cholinergic System of the Rat", *J. Neurosci. Res.*, 24, 276–285 (1989).

G. P. Vincent et al., "the Effects of Huperzine A, An Acetylcholinesterase Inhibitor, on the Enhancement of Memory in Mice, Rats and Monkeys", *Neurosci. Abst.*, 13, 884, Abstract No. 237.4 (1987).

R. J. Wurtman, "Alzheimer's Disease", *Scientific Amer.*, 62–66, 71–74 (1985).

(List continued on next page.)

*Primary Examiner*—Alan L. Rotman
*Attorney, Agent, or Firm*—Schwegman, Lundberg, Woessner & Kluth, P.A.

[57] ABSTRACT

The present invention provides $C^{10}$-mono- and disubstituted analogs of huperzine A which are active as acetylcholinesterase inhibitors, as well as intermediates for the preparation thereof.

15 Claims, 3 Drawing Sheets

OTHER PUBLICATIONS

Y. Xia et al., "Synthesis of the Benzenoid Analogue of the Chinese Nootropic Agent Huperzine A", *Tetrahedron Letters*, 30, 3291–3294 (1989).

Y. Xia et al., "A Practical Synthesis of the Chinese Nootropic Agent Huperzine A: A Possible Lead in the Treatment of Alzheimer's Disease", *J. Am. Chem. Soc.*, 111, 4116–4117 (1989).

C-10 ANALOGS OF HUPERZINE A

BACKGROUND OF THE INVENTION

Alzheimer's disease (AD) affects approximately 5–15% of the population of the U.S. over age 65 (1.24 million). This disease is frequently associated with individuals over the age of 60 and is the most frequent cause of institutionalization for long-term care. In 1983, more than $27 billion was spent in the U.S. in health care for Alzheimer's afflicted individuals.

Six basic areas of investigation have been defined by R. J. Wurtman, *Scientific Amer.*, 62 (1985), as underlying most research on the causes of Alzheimer's disease. These areas include faulty genes, accumulations of amyloid protein, infectious agents, environmental toxins (e.g., aluminum and certain unusual amino acids), inadequate blood flow and energy metabolism, and lastly, cholinergic deficits.

A number of possible therapeutic interventions are currently under study. These include the use of nerve growth factors (NGF), muscarinic and nicotinic agonists, acetylcholinesterase (ACHE) inhibitors, GABA-inverse agonists, NMDA modulators, and others. It is, however, unlikely that any single drug will restore cognition, especially in view of the involvement of a number of different neurotransmitter systems in memory processing, and the fact that dead neurons cannot be replaced.

To the extent that ACHE inhibitors can serve as useful adjuncts in the treatment of AD, two relatively new lycopodium alkaloids, huperzine A and B, isolated from *Huperzia serrata* (Thunb.) Trev., a Chinese folk medicine, appear superior to THA and physostigmine. J. S. Liu et al., *Can. J. Chem.*, 64, 837 (1986); W. A. Ayer et al., ibid., 67, 1077 (1989), ibid., 67, 1538 (1989). The structure of huperzine A is depicted below:

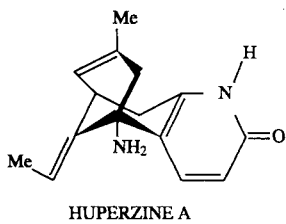

HUPERZINE A

In studies performed in China, these compounds have been found to improve memory and learning in animals. X. C. Tang et al., *Acta Pharmacol. Sinica*, 7, 507 (1986). Additionally, huperzine A has been studied by workers at Hoffmann LaRoche in mice and squirrel monkeys, and the compound has been found to be an effective cognition enhancer. G. P. Vincent et al., *Neurosci. Abst.*, 13, 884 (1987). The duration of action of a single dose (2 mg/kg i.m.) of huperzine A is over 6 hr, a remarkable result in relation to the AChE inhibitory action of physostigmine (0.65 mg/kg i.m.), which has a maximal duration of action of 60 min and which causes considerable side effects. X. C. Tang et al., *J. Neurosci. Res.*, 24, 276 (1989). Huperzine A has been further tested in 128 patients suffering from myasthenia gravis and found to control the clinical manifestations of the disease in 99% of these cases. Y. S. Cheng, *New Drugs and Clinical Remedies*, 5, 197 (1986).

Analogs of huperzine A have been reported. For example, A. P. Kozikowski et al. (U.S. Pat. No. 4,929,731) disclose the analog of huperzine A, wherein the amino group has been replaced by —$CH_2NH_2$. However, this analog was about 166 times less potent than (±)-huperzine A as an inhibitor of AChE. A. P. Kozikowski (U.S. Pat. No. 5,104,880) discloses analogs of huperzine A wherein the $C^8$–$C^{15}$ double bond and the $C_{15}$-methyl group are absent. However, these analogs also exhibited less AChE inhibitory activity than (−)-huperzine A.

Therefore, a continuing need exists for analogs of huperzine which exhibit improved potency, high metabolic stability, better partitioning into the brain, and/or a longer duration of action.

SUMMARY OF THE INVENTION

The present invention provides compounds of general formula (I), which are $C^{10}$-substituted derivatives of huperzine A:

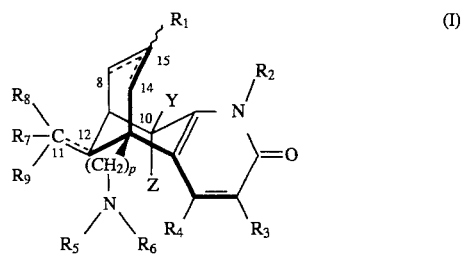

wherein one of Y and Z is H or ($C_1$–$C_8$)alkyl and the other of Y and Z is ($C_1$–$C_8$)alkyl, vinyl, ($C_3$–$C_8$)alkenyl, ethynyl, CN, $NO_2$, halo, OR', SR', $CO_2R'$, C(O)N(R')$_2$, C(O)R', S(O)R' or $SO_2R'$, wherein R' is H, ($C_1$–$C_4$)alkyl or phenyl, optionally substituted by 1–2 X, wherein X is halo, $CF_3$, $OR_{12}$, $SR_{12}$, CN, $NO_2$, $CO_2R_{12}$, C(O)N($R_{12}$)$_2$, S(O)$R_{12}$ or $SO_2R_{12}$, wherein each $R_{12}$ is H, $CF_3$, phenyl or ($C_1$–$C_4$)alkyl; or Y and Z together are —(CH$_2$)$_n$— wherein n is 2–3, carbonyl (=O) or =C($R_{10}$)($R_{11}$) wherein each of $R_{10}$ and $R_{11}$ is H, X or ($C_1$–$C_4$)alkyl; p is 0 or 1; $R_1$ is H, ($C_1$–$C_8$)alkyl or halo; $R_2$ is H or ($C_1$–$C_8$)alkyl; $R_3$ and $R_4$ are individually H, ($C_1$–$C_8$)alkyl, $NO_2$, hydroxy or halo; $R_5$ and $R_6$ are individually H, ($C_1$–$C_8$)alkyl, aryl or aralkyl; $R_7$ is H, halo or ($C_1$–$C_8$)alkyl, $R_8$ is halo or ($C_1$–$C_8$)alkyl; $R_9$ is absent or is H; and the bonds represented by = are individually single or double bonds (C=C), and the pharmaceutically acceptable salts thereof.

Therefore, the genus of compounds of formula I does not include huperzine A itself, or the simple N-alkylated derivatives thereof. Preferably, one of Y or Z is ($C_1$–$C_4$)alkyl, allyl, or ($C_1$–$C_4$)alkyl substituted by X, e.g., $CH_2X$, and the other of Y or Z is H or ($C_1$–$C_4$)alkyl. Preferably, $R_1$ is H, halo (Cl, Br, I or F, most preferably F) or methyl. Preferably, $R_2$ is H, preferably $R_3$ is H, nitro or halo, preferably $R_4$ is H, ($C_1$–$C_4$)alkyl or OH, and preferably $R_5$ and $R_6$ are H. Preferably $R_7$ and $R_9$ are H, and $R_8$ is ($C_1$–$C_4$)alkyl, preferably $CH_3$. Preferably, at least one of the bonds represented by = is a single bond. Of come, $C^8$–$C^{15}$ and $C^{14}$–$C^{15}$ cannot both be connected by C=C. Therefore, the preferred compounds of formula I are huperzine A analogs which are mono- or bis-substituted at $C^{10}$, or are mono- or bis-substituted $C^{10}$ analogs of dihydro or bis(dihydro)analogs of huperzine A which can also comprise substituents on the pyridone ring, or are C-10 analogs of pyridone ring-substituted analogs of huperzine A.

The compounds of the general formula I may exist in the form of optical isomers, and these isomers, as well as racemic (±) mixtures are included within the invention. The present invention also includes both the 10R and 10S, both the 12R and 12S, and both the 15R and 15S enantiomers of the present compounds, as well as unresolved or partially resolved mixtures thereof. The term "alkyl" includes linear or branched alkyl, cycloalkyl or (cycloalkyl)alkyl. Preferably, alkyl is $(C_1-C_4)$alkyl. The terms "aryl" and "aralkyl" are preferably $(C_6-C_{12})$aryl or $(C_7-C_{19})$aralkyl. Preferred aryl groups include phenyl (Ph), tolyl, xylyl, anisyl and the like. Preferred aralkyl groups include aryl$(C_1-C_3)$alkyl moieties.

The $C^{15}$—$R_1$ bond is waved to indicate that the $R_1$ substituent, when present, may be equatorial or axial, or a mixture thereof. Although for convenience, the $C^{11}$-$C^{12}$ bond is positioned equatorially, it may be either equatorial, axial, or a mixture thereof. Of the $C^{10}$ substituents, it is preferred that Y be H or $CH_3$, most preferably H, and that Z be $(C_1-C_4)$alkyl, or allyl, most preferably $CH_3$.

The structures of some preferred embodiments of the invention and their bioactivity are summarized in Table I, below.

DETAILED DESCRIPTION OF THE INVENTION

Compounds of formula I can be readily prepared from the versatile intermediate compound (II):

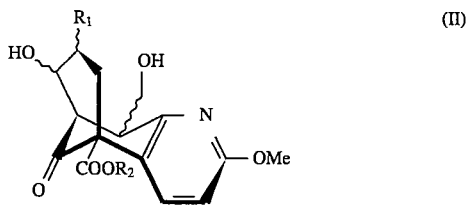

wherein $R_1$ and $R_2$ are as defined hereinabove. For example, the deshydroxymethyl analog of this compound wherein $R_1$ and $R_2$ are methyl is disclosed as compound 19 (R=H) at FIG. 2 of U.S. Pat. No. 5,104,880 and as the compounds of formula (I), $R_3^3$ and $R_3^2$=H or $(C_1-C_8)$alkyl, and $R_3^1$=H and $(C_1-C_8)$alkoxy in U.S. Pat. No. 4,929,731. Thus, while the

TABLE I

| Compound No. | X | Y | $R_1$ | $R_2$–$R_7$, $R_9$ | $R_8$ | $C^8$–$C^{15}$ [1] Dbl Bond | $C^{11}$–$C^{12}$ [1] Dbl Bond | FBS AChE $K_i$ (μM)* |
|---|---|---|---|---|---|---|---|---|
| (±)Huperzine A | H | H | $CH_3$ | H | $CH_3$ | + | + | 0.02 ± 0.005 |
| 8b | Me | H | $CH_3$ | H | $CH_3$ | + | + | 0.008 ± 0.002 |
| 8c | Et | H | $CH_3$ | H | $CH_3$ | + | + | 2.04 + 0.48 |
| 8d | n-Pr | H | $CH_3$ | H | $CH_3$ | + | + | 207 |
| 8a | allyl | H | $CH_3$ | H | $CH_3$ | + | + | 275 |
| 8e | n-Bu | H | $CH_3$ | H | $CH_3$ | + | + | 192 |

[1](+) = Double bond is present
*Dissociation constant ($K_i$) for inhibition of AChE determined according to the procedure of Y. Ashani et al., Molecular Pharmacol., 45, 555 (1994).

Thus, the compounds of formula I, or mixtures thereof, are useful as inhibitors of acetylcholinestemse (ACHE), and thus may be useful in clinical settings, for the treatment of memory and learning disorders. Such conditions include Alzheimer's dementia (AD), and other age-related memory impairments. While it is known that defects in neurotransmitter systems other than the cholinergic system play a role in the memory loss associated with AD, findings by K. L. Davis, presented at "New Strategies for the Treatment of Alzheimer's Disease," NIA meeting (Jan. 8–10, 1990) indicate that ACHE inhibitors, such as physostigmine, do lead to modest cognitive improvement, and may prove useful in combination with other drugs, e.g., clonidine, deprenyl or desipmmine. Specifically, the use of at least one compound of formula I, in combination with an efficacious M2 antagonist which facilitates acetylcholine release, may constitute an effective therapeutic strategy.

All percentages given herein are by weight unless otherwise noted.

BRIEF DESCRIPTION OF THE DRAWINGS

FIG. 2 is a schematic depiction of the synthesis of the $C^{10}$-alkylhuperzine A intermediate 7a.

synthesis of the compounds of formula I of the invention is primarily exemplified by reference to compounds wherein $R_1$–$R_7$ and $R_9$ are H, p=0 $R_8$ is $CH_3$, the synthesis of compounds of formula I wherein $R_1$–$R_9$ are varied as disclosed above can be accomplished from the compounds of formula II as disclosed in U.S. Pat. Nos. 5,104,880 and 4,929,731, the disclosures of which are specifically incorporated by reference herein.

Likewise, other of the present compounds of formula I can be prepared via methodologies disclosed in U.S. Pat. No. 5,104,880 from the 8-substituted-5,6,7,8-tetrahydro-2-methoxy-6-oxo-5-quinolinecarboxylic acid methyl ester, shown as formula III below:

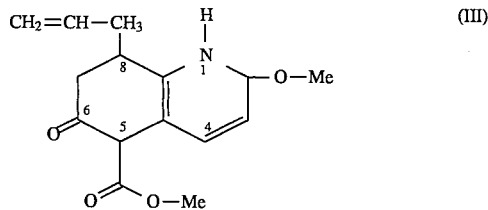

This compound, wherein Y=Z=H, disclosed as compound II in U.S. Pat. No. 4,929,731 (keto form) and as compound 18 in U.S. Pat. No. 5,104,880, wherein it is converted into the compound of formula II, wherein $R_1$=$R_2$=$CH_3$ in one step by reaction with methacrolein and tetramethylguanidine (TMG).

Figure 1:
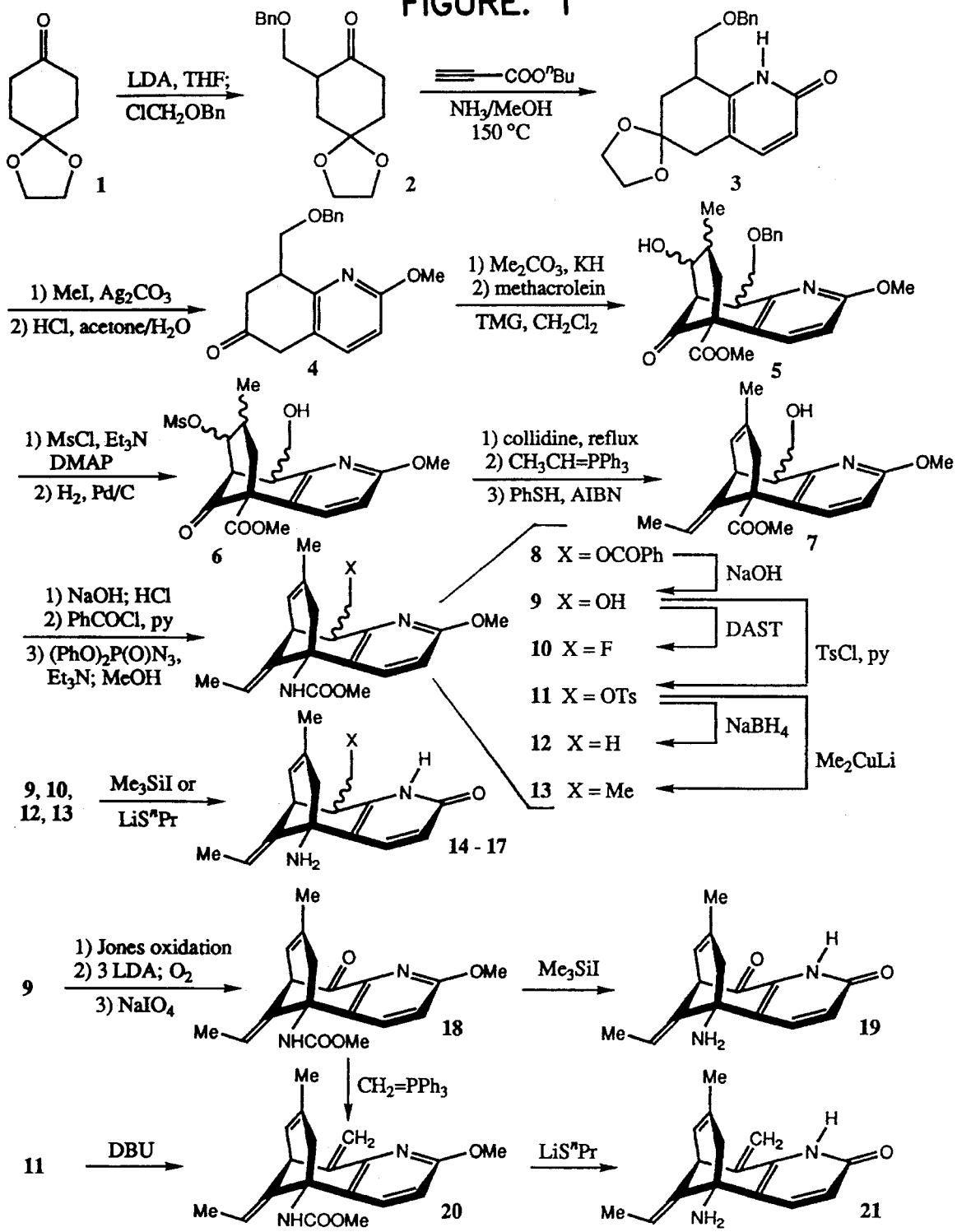
FIG. 1 is a schematic depiction of the synthesis of compounds 14–17, 19 and 21 of formula I.

More specifically, a general scheme for the preparation of the present compounds of formula (I) via a compound of formula (II) wherein $R_1$ and $R_2$ are methyl, is depicted in FIG. 1. In accord with FIG. 1, compound 1 is alpha-benzyloxymethylated with benzyloxy(chloro)methane and then reacted with an alkyl propiolate to yield 1H-quinolin- 2-one (3), which is methylated and deprotected to yield 5H-quinoline (4). Compound 4 is alpha-methoxycarbonylated and then cyclized with $CH_2=CH(CH_3)CHO$ to yield compound 5, which is hydrogenolyzed and mesylated (MsCl, $Et_3N$) to yield 6. Elimination of MsOH, followed by a Wittig reaction with $CH_3CH=PPh_3$ and inversion of the double bond from predominantly Z to predominantly E stereochemistry affords 7. Intermediate 7 is saponified, benzoylated and converted to the methoxycarbonylamino intermediate 8, which can be deprotected to yield 14 (X=OH). Alternatively, prior to decarbomethoxylation to yield the free amine, the compound 9 can be convened to compounds 10–13 which, in turn, yield the corresponding compounds of formula I (15–17) wherein Y=H and $Z=XCH_2$, wherein X is F, H or $CH_3$, respectively.

Likewise, as shown in FIG. 1, the hydroxymethyl intermediate 9 can be converted into $C^{10}$-keto analog 18 or $C^{10}$-methylene analog 20, which can be decarbomethoxylated to yield compounds 19 and 21, respectively. Likewise, triflated compound 11 can be converted directly to $C^{10}$-methylene analog 20, by reaction with DBU.

Figure 2:
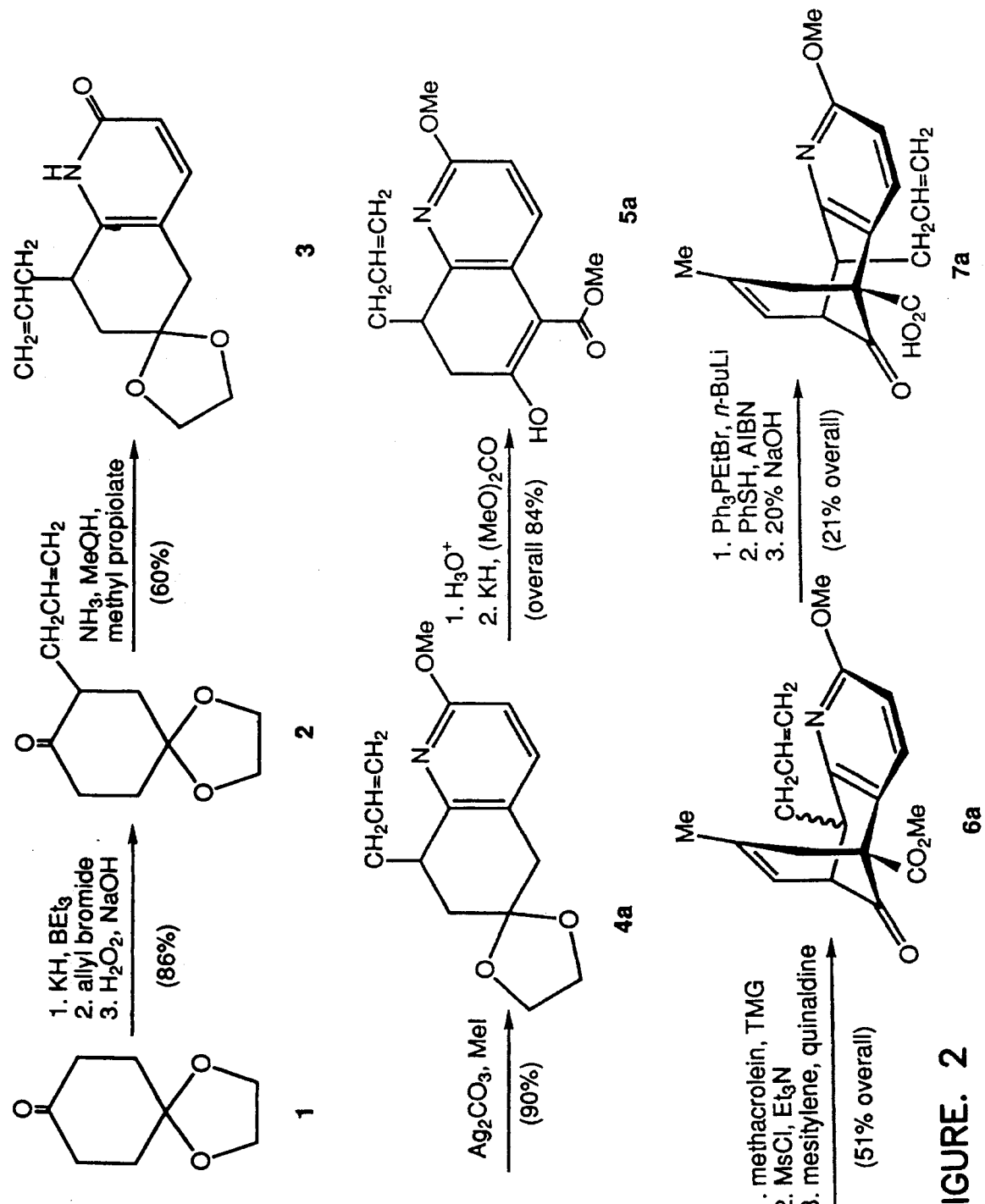
Figure 3:
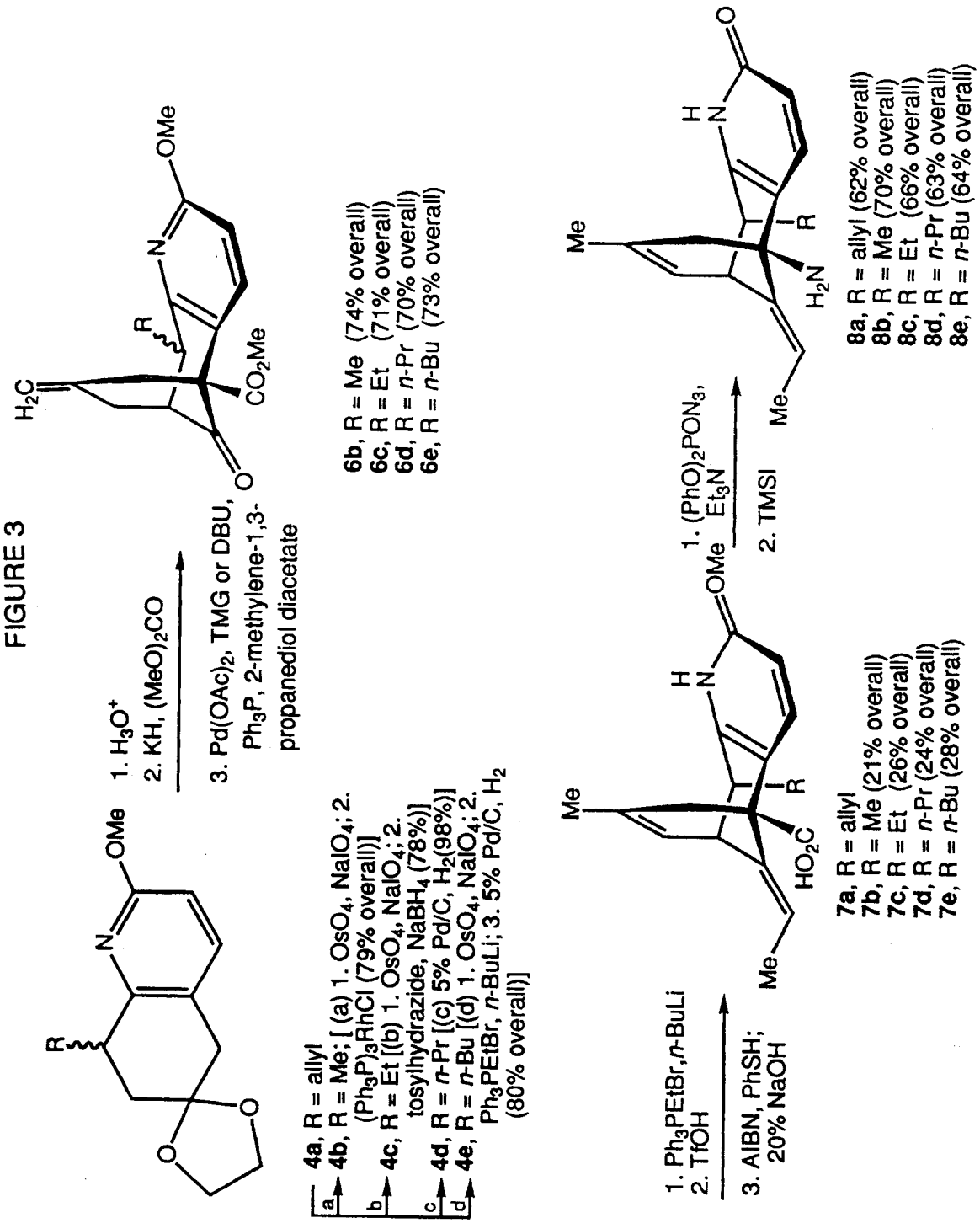
FIG. 3 is a schematic depiction of the synthesis of compounds 8a–8e of formula I.

Using the reactions outlined in FIG. 1, 2-allyl-4-ethylenedioxy cyclohexanone (2a) can be converted into the $C^{10}$-allylhuperzine intermediate 7a, as shown in FIG. 2. Likewise, the allyl substituent in intermediate 4a can be converted into a $(C_1-C_4)$alkyl group as shown in FIG. 3. The alkylated intermediates 4b–4e were converted to $C^{10}$-alkylated huperzine intermediates 7b–7e which, along with 2a, can be converted to the compounds of formula I (8a–8e) in two steps.

In an analogous fashion, 10,10-dimethylhuperzine can be prepared from 2,2-dimethyl-1,4-cyclohexanedione 4-monoethyleneketal, a compound prepared by L. A. K. Nelson et al., *Tetrahedron*, 47, 3259 (1991). As shown in Scheme 1, the spirocyclopropane analog 26 can be prepared from compound 25. Compound 25 can be prepared from 1,4-cyclohexanedione monoethyleneketal (1) by alpha-aminomethylation, followed by ring closure, as disclosed by Schering A.-G., Neth. Appl. 6,400,112, Jul. 23, 1964 (*Chem. Abstr.*, 62, 6542a (1965)), or directly as disclosed by S. M. Ruder et al., *Tet. Lett.*, 25, 5501 (1984).

Mono- or disubstituted bridgehead amino compounds of formula I, wherein $R_5$ and $R_6$ are $(C_1-C_8)$alkyl, aryl, aralkyl or mixtures thereof with H, can be prepared by conventional methods for the conversion of primary amino groups to secondary or tertiary amino groups. For example, see I. T. Harrison et al., *Compendium of Organic Synthetic Methods*, Wiley-Interscience, New York (1971) at pages 240–246.

Pharmaceutically acceptable acid salts of the present compounds can be prepared as described in U.S. Pat. No. 4,383,114.

The compounds of formula I can be employed, singly or in combination, in an amount effective to inhibit the cholinesterase enzymes (such as AChE) in a mammal (such as a human) in need of such treatment. Therefore, the present invention also includes a pharmaceutical composition, such as one or more unit dosage forms, of an effective enzyme-inhibiting amount of one or more of the compounds of formula I in combination with a pharmaceutically acceptable carrier therefor. Such compositions can be administered orally or parenterally, including via intravenous, intramuscular, intraperitoneal, subcutaneous or topical administration.

For oral use of a compound of general formula 1, said compound can be administered, for example, in the form of tablets or capsules, or as an aqueous solution or suspension. In the case of tablets for oral use, carriers which are commonly used include lactose, mannitol, and corn starch, and lubricating agents, such as magnesium stearate, are commonly added. For oral administration in capsule form, the compound can be administered in dry form in a hard gelatin capsule or in a suitable gelled or liquid vehicle, such as a liquid polyethylene glycol or a carrageenan gel, in a soft gelatin capsule. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparations isotonic.

Scheme 1

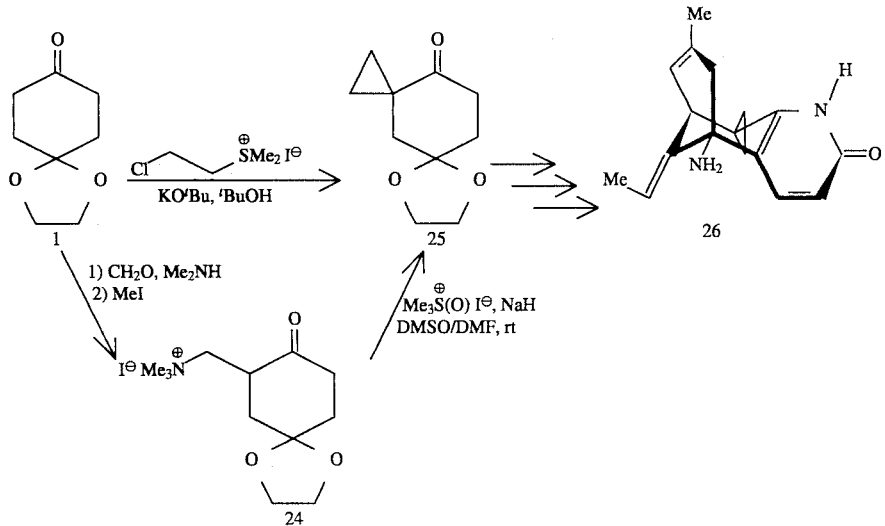

When a compound according to general formula I is used to treat a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 1 mg/kg of body weight, and preferably, of from 0.1 mg/kg to about 0.5 mg/kg of body weight, administered in single or divided doses. In some cases, however, it may be necessary to use dosages outside these limits.

The invention will be further described by reference to the following detailed examples, wherein h=hours, rt=20°–25° C. and tetrahydrofuran (THF) was distilled over sodium benzophenone ketyl. Toluene, triethylamine, and methylene chloride were distilled over calcium hydride. All other reagents were used as supplied unless otherwise stated. Silica gel 60 (Merck, 230–400 mesh for flash chromatography) was used for column chromatography. Infrared spectra were obtained on a Mattson 2020 FT-IR spectrometer. $^1$H and $^{13}$C NMR spectra were recorded in CDCl$_3$ on a Bruker AC-300 instrument (proton frequency 300 MHz) with the solvent signal ($\delta$=7.26 ppm and 77 ppm, respectively) as internal standard. The following abbreviations are used: br=broad, d=doublet, m=multiplet, q=quartet, s=singlet, and t=triplet. Low-resolution mass spectra were determined on a Hewlett-Packard 5971A spectrometer, and high-resolution mass spectra on a VG 70-SE double focusing magnetic sector spectrometer. The abbreviation "h" designates hours.

EXAMPLE 1

2-Allyl-4-ethylenedioxycyclohexanone (2)

A solution of 1,4-cyclohexanedione monoethylene ketal (9.37 g, 60 mmol) in THF (50 mL) was added to a suspension of KH (2.57 g, 63 mmol) in THF (200 mL) at rt under argon. After being stirred at rt (25° C.) for 30 min, the mixture was cooled to 0° C., and triethylborane (75 mL of 1M solution in THF) was added. The mixture was stirred for 30 min prior to the introduction of allyl bromide (7.8 mL, 90 mmol). After 1 h, H$_2$O$_2$ (30%, 50 mL) and NaOH (3M, 50 mL) were added at 0° C., and stirring was continued for 30 min at rt prior to removal of THF by rotary evaporation. The aqueous residue was extracted with ethyl acetate, washed with brine, dried over MgSO$_4$, and concentrated. Flash chromatography (30% ethyl acetate in hexanes) gave 10.1 g (86%) of 2 as an oil: IR (neat) 2957, 2887, 1714, 1438, 1140, 1049 cm$^{-1}$; $^1$H NMR $\delta$5.72 (m, 1H), 5.02 (m, 2H), 4.01 (m, 4H), 2.65 (m, 3H), 2.46 (m, 1H), 2.05 (m, 4H); $^{13}$C NMR $\delta$210.6, 135.7, 116.6, 107.3, 64.6, 64.4, 45.7, 39.8, 38.0, 34.4, 33.1; MS m/z 196 (M$^{30}$), 168, 155, 99.

EXAMPLE 2

8'-Allyl-1',5',7',8'-tetrahydrospiro[1,3-dioxolane-2,6'(2'H)-quinolin]-2'-one (3)

A mixture of 2 (1.96 g, 10 mmol), methyl propiolate (1.68 g, 20 mmol), and 40 mL of ammonia-saturated methanol in a 300 mL stainless steel Parr reaction vessel was heated to 150° C. for 6 h. After cooling, the solvent was removed under reduced pressure, and the crude product was purified by flash chromatography with 3% MeOH in CH$_2$Cl$_2$ as the eluent to afford 2.96 g (60%) of the pyridone 3: R$_f$=0.40 (10% MeOH in CH$_2$Cl$_2$); IR (KBr) 3448, 2887, 1649, 1618, 1093 cm$^{-1}$; $^1$H NMR $\delta$6.38 (d, 1H, J=9.3 Hz), 5.75 (m, 1H), 5.11 (m, 2H), 3.97 (m, 3H), 3.10 (m, 1H), 2.70 (m, 4H), 1.85 (m, 2H); $^{13}$C NMR $\delta$164.7, 143.9, 143.2, 118.1, 118.0, 111.8, 107.4, 64.6, 64.4, 37.6, 36.8, 35.8, 34.8.

EXAMPLE 3

8'-Allyl-7',8'-dihydro-2'-methoxyspiro[1,3-dioxolane-2,6'(5'H)quinoline] (4a)

A mixture of Ag$_2$CO$_3$ (7.17 g, 26.2 mmol), pyridone 3 (5.4 g, 21.9 mmol), and iodomethane (8.0 mL, 131 mmol) in 200 mL of CHCl$_3$ was refluxed in the dark with stirring. After cooling, filtration, and concentration, the residue was purified by flash chromatography with 25% ethyl acetate in hexanes as the eluent to afford 5.14 g (90%) of 4a: IR (neat) 2953, 1589, 1487, 830 cm$^{-1}$; $^1$H NMR $\delta$7.22 (d, 1H, J=8.2 Hz), 6.52 (d, 1H, J=8.2 Hz), 5.80 (m, 1H), 5.03 (m, 2H), 4.01 (m, 4H), 3.89 (s, 3H), 3.11 (m, 1H), 2.96 (m, 2H), 2.80 (dd, 1H, J=16.0, 2.4 Hz), 2.50 (m, 1H), 2.06 (m, 1H), 1.80 (dd, 1H, J=13.2, 10.9 Hz); $^{13}$C NMR $\delta$162.0, 154.5, 139.7, 137.1, 121.6, 116.3, 108.1, 107.9, 64.5, 64.4, 53.1, 39.4, 38.1, 38.0, 36.6; MS m/z 261 (M$^+$), 246, 220, 174, 148.

EXAMPLE 4

7',8'-Dihydro-2'-methoxy-8'-methylspiro[1,3-dioxolane-2,6'(5'H)quinoline] (4b)

To a solution of 4a (106 mg, 0.405 mmol) and 0.2 mL of 4% aqueous OsO$_4$ in 6 mL of dioxane-water (1:1) was added NaIO$_4$ (173 mg, 0.81 mmol) at rt, and the resulting mixture was stirred for 0.5 h. The dioxane was removed by rotary evaporation, and the aqueous residue was extracted with ethyl acetate. The extracts were washed with brine, dried, and concentrated. Flash chromatography (20% ethyl acetate in hexanes) gave 105 mg of the aldehyde. To a solution of this aldehyde (105 mg, 0.4 mmol) in 5 mL of benzene was added (Ph$_3$P)$_3$RhCl (444 mg, 0.48 mmol) at rt under argon, and the mixture was refluxed for 24 h. Filtration, concentration, and flash chromatography (20% ethyl acetate in hexanes) gave 80 mg (79% overall) of 4b: R$_f$=0.37 (20% ethyl acetate in hexane); IR (neat) 2955, 2879, 1579, 1477, 1078, 819 cm$^{-1}$; $^1$H NMR $\delta$7.19 (d, 1H, J=8.3 Hz), 6.49 (d, 1H, J=8.3 Hz), 4.00 (m, 4H), 3.89 (s, 3H), 3.09 (m, 1H), 2.98 (d, 1H, J=16.2 Hz), 2.79 (d, 1H, J=16.2 Hz), 2.10 (m, 1H), 1.73 (dd, 1H, J=13.0, 11.0 Hz), 1.42 (d, 3H) J=6.9 Hz); $^{13}$C NMR $\delta$161.9, 156.1, 139.5, 120.8, 107.8, 107.5, 64.4, 52.9, 40.1, 38.1, 34.8, 19.6; MS m/z 235 (M$^+$), 220, 163, 148.

EXAMPLE 5

8'-Ethyl-7',8'-dihydro-2'-methoxyspiro[1,3-dioxolane-2,6'(5'H)quinoline] (4c)

To a solution of 4a (1.06 g, 4.05 mmol) and 2 mL of 4% aqueous OsO$_4$ in 60 mL of dioxane-water (1:1) was added NaIO$_4$ (1.73 g, 8.1 mmol) at rt, and the resulting mixture was stirred for 0.5 h. The dioxane was removed by rotary evaporation, and the aqueous residue was extracted with ethyl acetate. The extracts were washed with brine, dried, and concentrated. Flash chromatography (20% ethyl acetate in hexanes) gave 1.04 g of aldehyde. A mixture of this aldehyde (1.04 g, 3.97 mmol) and tosylhydrazide (1.04 g, 5.6 mmol) in 15 mL of MeOH was refluxed for 3 h and then cooled to 0° C. NaBH$_4$ (3.33 g, 88 mmol) was added within 1 h at 0° C., and the mixture was refluxed for 18 h. The reaction was quenched with water. The MeOH was removed by rotary evaporation, and the aqueous residue was extracted with ethyl acetate. The extracts were washed with brine, dried, and concentrated. Flash chromatography (20% ethyl acetate in hexanes) gave 800 mg (78% overall) of 4c: IR (neat) 2953, 1599, 1579, 1477, 1078, 993 cm$^{-1}$; $^1$H NMR δ7.20 (d, 1H, J=8.3 Hz), 6.50 (d, 1H, J=8.3 Hz), 4.01 (m, 4H), 3.88 (s, 3H), 2.98 (m, 2H), 2.78 (dd, 1H, J=16.0, 2.3 Hz), 2.25 (m, 1H), 2.12 (m, 1H), 1.73 (m, 2H), 0.95 (t, 3H) J=7.5 Hz); $^{13}$C NMR δ161.9, 155.4 139.6, 121.4, 107.9, 107.8, 64.4, 53.0, 40.9, 38.0, 36.5, 26.3, 11.0; MS m/z 249 (M$^+$), 220, 162, 148.

EXAMPLE 6

7',8'-Dihydro-2'-methoxy-8'-propylspiro [1,3-dioxolane-2,6'(5'H)quinoline] (4d)

A solution of 4a (1.04 g, 4 mmol) in 100 mL of EtOH was hydrogenated at 60 psi hydrogen pressure (Parr shaker) over 200 mg of 5% Pd/C for 5 h. Filtration, concentration, and flash chromatography of the residue (30% ethyl acetate in hexanes) gave 1.03 g (98%) of 4d: IR (neat) 2955, 1599, 1477, 1084, 1031 cm$^{-1}$; $^1$H NMR δ7.20 (d, 1H, J=8.3 Hz), 6.50 (d, 1H, J=8.3 Hz), 4.01 (m, 4H), 3.89 (s, 3H), 2.98 (m, 2H), 2.78 (dd, 1H, J=16.0, 2.4 Hz), 2.01 (m, 2H), 1.67 (m, 2H), 1.40 (m, 2H), 0.96 (t, 3H, J=7.2 Hz); $^{13}$C NMR δ162.0, 155.7, 139.6, 121.3, 107.9, 107.7, 64.4, 53.0, 39.5, 38.0, 37.2, 35.9, 19.9, 14.3; MS m/z 263 (M$^+$).

EXAMPLE 7

8'-Butyl-7',8'-dihyro-2'-methoxyspiro [1,3-dioxolane-2,6'(5'H()quinoline] (4e)

To a solution of 4a (1.04 g, 4 mmol) and 2 mL of 4% aqueous OsO$_4$ in 60 mL of dioxane-water (1:1) was added NaIO$_4$ (1.88 g, 8.8 mmol) at rt, and the resulting mixture was stirred for 0.5 h. The dioxane was removed by rotary evaporation, and the aqueous residue was extracted with ethyl acetate. The extracts were washed with brine, dried, and concentrated. Flash chromatography (20% ethyl acetate in hexanes) gave 1.05 g of the aldehyde. To a suspension of ethyltriphenylphosphonium bromide (6.98 g, 18.8 mmol) in dry THF (15 mL) was added n-BuLi (6.4 mL, 16 mmol, 2.5M in hexane) within 10 min. The resulting suspension was stirred at rt for 1 h and then cooled to 0° C. A solution of the above aldehyde (1.05 g, 3.99 mmol) in 5 mL of dry THF was added over a period of 10 min. The resulting mixture was allowed to warm to rt and stirred at rt for 2 h. The reaction was quenched with water, the THF was removed by rotary evaporation, and the aqueous residue was extracted with ethyl acetate. The organic layers were washed with brine, dried, and concentrated. Flash chromatography (8% ethyl acetate in hexane) gave 935 mg of the Z olefination product. A solution of this olefin (935 mg, 3.4 mmol) in 100 mL of EtOH was hydrogenated at 60 psi hydrogen pressure (Parr shaker) over 200 mg of 5% Pd/C for 4 h. Filtration, concentration, and flash chromatography of the residue (30% ethyl acetate in hexanes) gave 886 mg (80%) of 4e: IR (neat) 2953, 1599, 1475, 1313, 1085, 1033 cm$^{-1}$; $^1$H NMR δ7.20 (d, 1H, J=8.4 Hz), 6.50 (d, 1H, J=8.4 Hz), 4.01 (m, 4H), 3.88 (s, 3H), 2.97 (m, 2H), 2.78 (dd, 1H, J=15.9, 2.3 Hz), 2.09 (m, 1H), 1.76 (m, 1H), 1.35 (m, 4H), 0.95 (t, 3H) J=7.2 Hz); $^{13}$C NMR δ161.9, 155.7, 139.6, 121.3, 108.0, 107.7, 64.5, 53.0, 39.6, 38.0, 37.2, 28.9, 22.9, 14.1; MS m/z 277 (M$^+$), 234, 1221, 191, 148.

EXAMPLE 8

8-Allyl-5,6,7,8-tetrahydro-2-methoxy-6-oxo-5-quinolinecarboxylic Acid Methyl Ester (5)

A solution of 4a (1.31 g, 5 mmol) in 30 mL of 5% HCl-acetone (1:1) was refluxed for 3 h. Acetone was removed on a rotary evaporator, and the aqueous layer was basified with solid NaHCO$_3$. The resulting mixture was extracted with ethyl acetate. The organic extracts were washed with brine, dried, and filtered. Concentration and flash chromatography (20% ethyl acetate in hexanes) gave 1.02 g of the ketone. This ketone (1.02 g, 4.7 mmol) in 10 mL of Me$_2$CO$_3$ was added dropwise to a suspension of KH (566 mg, 14.1 mmol) in 20 mL of Me$_2$CO$_3$ over 20 min under argon at reflux, and the resulting mixture was refluxed for an additional 20 min. The reaction was quenched with MeOH followed by saturated NH$_4$Cl. The solvent was removed under reduced pressure, and the residue was extracted with ethyl acetate. The ethyl acetate extracts were washed with brine, dried, and filtered. Concentration and flash chromatography (10% ethyl acetate in hexanes) gave 1.16 g (84%) of 5: IR (neat) 2935, 1641, 1601, 1477, 1303, 827 cm$^{-1}$; $^1$H NMR δ12.41 (s, 1H), 7.95 (d, 1H, J=8.7 Hz), 6.57 (d, 1H, J=8.7 Hz), 5.80 (m, 1H), 5.10 (m, 2H), 3.92 (s, 3H), 3.91 (s, 3H), 3.01 (m, 1H), 2.70 (m, 2H), 2.40 (m, 2H); $^{13}$C NMR δ175.6, 171.9, 161.1, 153.1, 136.3, 136.1, 119.3, 117.0, 107.2, 97.8, 53.3, 51.7, 38.9, 35.9, 33.2; MS m/z 275 (M$^+$).

EXAMPLE 9

10-Allyl-9,10-dihydro-2-methoxy-7-methyl-11-oxo-5,9-methanocycloocta[b]pyridine-5(6H)-carboxylic Acid Methyl Ester (6a)

To a solution of 5 (1.61 g, 5.87 mmol) and tetramethylguanidine (74 mL, 0.59 mmol) in 30 mL of CH$_2$Cl$_2$ was added methacrolein (1.96 mL, 23.6 mmol) at 0° C. The resulting mixture was allowed to warm to rt and stirred for 8 h. Concentration and flash chromatography (40% ethyl acetate in hexanes) gave 1.92 g of the aldol intermediate. To a solution of the above alcohol (1.92 g, 5.57 mmol), NEt$_3$ (1.0 mL, 7.2 mmol), and DMAP (17 mg, 0.14 mmol) in 20 mL of CH$_2$Cl$_2$ was added dropwise MsCl (515 mL, 6.68 mmol) within 30 min at 0° C. Stirring was continued at rt for 4 h. The reaction mixture was diluted with CH$_2$Cl$_2$, washed with saturated NaHCO$_3$ and brine, dried over MgSO$_4$, and concentrated. The crude product was purified by flash chromatography (40% ethyl acetate in hexanes) to afford 2.12 g of the mesylate. A mixture of this mesylate (2.12 g, 5.02 mmol) and quinaldine (6.8 mL, 50 mmol) in 50 mL of mesitylene was refluxed under argon for 18 h. After cooling, the solvent was removed under reduced pressure, and the crude product was purified by flash chromatography with 20% ethyl acetate in hexanes as the eluent to afford 984 mg (51%) of 6a as a mixture of two diastereoisomers: IR (neat) 2951, 1745, 1720, 1601, 1263 cm$^{-1}$; $^1$H NMR (major isomer) δ7.09 (d, 1H, J=8.6 Hz), 6.58 (d, 1H, J=8.6 Hz), 5.81 (m, 1H), 5.34 (m, 2H), 5.10 (m, 2H), 3.88 (s, 3H), 3.74 (s, 3H), 3.34 (m, 1H), 3.5 (m, 1H), 2.58 (m, 1H), 2.10 (m, 1H), 1.53 (s, 3H); $^{13}$C NMR δ 207.0, 171.2, 171.1, 163.1, 162.6, 153.9, 152.7, 137.5, 137.2, 136.3, 135.3, 134.4, 133.1, 126.4, 125.4, 123.9, 119.8, 117.7, 116.7, 109.6, 80.7, 80.1, 53.2, 53.1, 52.4, 50.9, 48.7, 47.9, 47.0, 46.6, 39.0, 33.6, 22.2, 22.0; MS m/z 327 (M$^+$), 299, 198.

EXAMPLE 10

7,8,9,10-Tetrahydro-2-methoxy-10-methyl-7-methylene-11-oxo-5,9-methanocycloocta[b]pyridine-5(6H)-carboxylic Acid Methyl Ester (6b).

A mixture of 4b (1.89 g, 8.04 mmol) in 50 mL of 5% HCl-acetone (1:1) was refluxed for 3 h. Acetone was removed on a rotary evaporator, and the aqueous layer was basified with solid NaHCO$_3$. The resulting mixture was extracted with ethyl acetate. The organic extracts were washed with brine, dried, and filtered. Concentration and flash chromatography (20% ethyl acetate in hexanes) gave 1.47 g of ketone. This ketone (1.47 g, 7.72 mmol) in 10 mL of Me$_2$CO$_3$ was added dropwise to a mixture of KH (1.01 g, 25.2 mmol) in 40 mL of Me$_2$CO$_3$ over 20 min under argon at reflux, and the resulting mixture was refluxed for an additional 20 min. The reaction was quenched with MeOH followed by saturated NH$_4$Cl. The solvent was removed under reduced pressure, and the residue was extracted with ethyl acetate. The ethyl acetate extracts were washed with brine, dried, and filtered. Concentration and flash chromatography (10% ethyl acetate in hexanes) gave 1.73 g of the β-ketoester. A mixture of Pd(OAc)$_2$ (59 mg, 0.34 mmol) and Ph$_3$P (361 mg, 1.38 mmol) in 30 mL of dioxane was stirred at rt under argon for 30 min. To the complex thus obtained was added a solution of the above β-ketoester (1.73 g, 6.94 mmol), DBU (1.45 mL, 9.66 mmol), and 2-methylene-1,3-propanediol diacetate (1.25 mL, 7.2 mmol) in 20 mL of dry dioxane within 5 min. After stirring for 25 min at rt, additional DBU (0.69 mL, 0.55 mmol) was added dropwise. After stirring at rt for 30 min, the mixture was heated to 95° C. for 2 h. Concentration and flash chromatography (30% ethyl acetate in hexane) gave 1.74 g (74% overall) of 6b as a mixture of two diastereoisomers: IR (neat) 2953, 1739, 1720, 1601, 1577, 1427, 906, 756 cm$^{-1}$; $^1$H NMR (major isomer) δ6.90 (d, 1H, J=8.6 Hz), 6.50 (d, 1H, J=8.6 Hz), 4.68 (s, 1H), 4.36 (s, 1H), 3.81 (s, 3H), 3.71 (s, 3H), 3.14 (m, 2H), 2.70 (m, 2H), 2.50 (m, 2H), 1.22 (d, 3H) J=7.3 Hz); $^{13}$C NMR δ208.0, 207.9, 171.1, 171.0, 162.6, 162.3, 155.7, 154.5, 138.8, 138.7, 137.3, 136.9, 124.1, 123.2, 117.0, 116.9, 109.5, 109.3, 62.7, 62.0, 53.0, 52.9, 52.8, 52.3, 50.8, 47.8, 47.4, 46.4, 42.6, 40.4, 36.2, 22.8, 15.0; MS m/z 301 (M$^+$), 269, 246, 214.

EXAMPLE 11

10-Ethyl-7,8,9,10-tetrahydro-2-methoxy-7-methylene-11-oxo-5,9-methanocycloocta[b]pyridine-5(6H)-carboxylic Acid Methyl Ester (6c)

was prepared from 4c in the same manner as described for the preparation of compound 6b: IR (neat) 2953, 1743, 1724, 1601, 1577, 1479, 823 cm$^{-1}$; $^1$H NMR (major isomer) δ6.94 (d, 1H, J=8.7 Hz), 6.56 (d, 1H, J=8.7 Hz), 4.73 (s, 1H), 4.41 (s, 1H), 3.87 (s, 3H), 3.77 (s, 3H), 3.01 (m, 1H), 2.90 (m, 2H), 2.75 (m, 1H), 2.55 (m, 2H), 1.85 (m, 1H), 1.60 (m, 1H), 1.22 (t, 3H, J=7.4 Hz); $^{13}$C NMR δ209.0, 208.6, 171.5, 171.4, 162.9, 162.4, 155.2, 154.2, 139.3, 139.1, 137.3, 124.6, 124.2, 115.9, 115.7, 109.7, 62.9, 62.3, 53.4, 53.3, 53.0, 52.6, 50.0, 48.1, 47.6, 47.3, 43.5, 36.0, 29.9, 21.6, 11.6, 11.4; MS m/z 315 (M$^+$), 287, 256, 228.

EXAMPLE 12

7,8,9,10-Tetrahydo-2-methoxy-7-tetramthylene-10-propyl-11-oxo-5,9-methanocycloocta[b]pyridine-5(6H)-carboxylic Acid Methyl Ester (6d)

was prepared from 4d in the same manner as described for the preparation of compound 6b: IR (neat) 2955, 1743, 1724, 1601, 1477, 1263 cm$^{-1}$; $^1$H NMR (major isomer) δ6.92 (d, 1H, J=8.6 Hz), 6.53 (d, 1H, J=8.6 Hz), 4.70 (br s, 1H), 4.38 (br s, 1H), 3.85 (s, 3H), 3.75 (s, 3H), 3.10 (m, 2H), 2.80 (m, 2H), 2.55 (m, 2H), 1.66 (m, 1H), 1.40 (m, 3H), 0.85 (t, 3H, J=7.2 Hz); $^{13}$C NMR δ208.7, 208.3, 171.2, 162.7, 162.3, 155.3, 154.2, 139.1, 138.9, 137.1, 137.0, 124.4, 123.9, 115.6, 109.5, 109.4, 62.6, 62.1, 53.1, 52.4, 51.2, 50.3, 48.1, 48.0, 47.9, 45.2, 43.1, 39.0, 36.0, 30.7, 20.1, 19.8, 14.0, 13.8; MS m/z 329 (M$^+$), 287, 228.

EXAMPLE 13

10-Butyl-7,8,9,10-tetrahydro-2-methoxy-7-methylene-11-oxo-5,9-methanocycloocta[b]pyridine-5(6H)-carboxylic Acid Methyl Ester (6e)

was prepared from 4e in the same manner as described for the preparation of compound 6b: IR (neat) 2953, 1743, 1724, 1601, 1479, 1261, 1035 cm$^{-1}$; $^1$H NMR (major isomer) δ6.99 (d, 1H, J=8.4 Hz), 6.66 (d, 1H, J=8.4 Hz), 4.70 (s, 1H), 4.38 (s, 1H), 3.84 (s, 3H), 3.74 (s, 3H), 3.10 (m, 2H), 2.80 (m, 2H), 2.54 (m, 2H), 1.75–1.20 (m, 6H), 0.82 (t, 3H) J=7.0 Hz); $^{13}$C NMR δ 208.6, 208.2, 171.2, 162.6, 162.2, 155.2, 154.9, 139.1, 138.9, 137.1, 137.0, 124.4, 123.9, 115.5, 109.4, 109.3, 62.6, 62.0, 53.1, 52.3, 51.3, 50.2, 47.9, 47.8, 45.3, 43.1, 36.4, 36.0, 29.0, 28.8, 28.1, 22.5, 22.3, 13.8, 13.7; MS m/z 343 (M$^+$), 300, 287, 228.

EXAMPLE 14

(11E)-10-Allyl-11-ethylidene-9,10-dihydro-2-methoxy-7-methyl-5,9-methanocycloocta[b]pyridine-5(6H)-carboxylic Acid (7a)

To a suspension of ethyltriphenylphosphonium bromide (5.24 g, 14.1 mmol) in dry THF (50 mL), n-BuLi (4.8 mL, 12 mmol, 2.5M in hexane) was added within 10 min. The reaction mixture was stirred at rt for 1 h and then cooled to 0° C. A solution of β-ketoester 6a (981 mg, 3.0 mmol) in dry THF (10 mL) was added dropwise over a period of 15 min. The resulting mixture was allowed to warm to rt and stirred for an additional 3 h. The reaction was quenched with water, the THF was removed by rotary evaporation, and the aqueous residue was extracted with ethyl acetate. The extracts were washed with brine, dried, and concentrated. Flash chromatography (5% and then 10% ethyl acetate in hexane) gave 864 mg of the Z olefmation product. To a solution of this olefin (864 mg, 2.55 mmol) in dry toluene (10 mL) were added azobis(isobutyronitrile) (418 mg, 2.55 mmol) and thiophenol (0.52 mL, 5.1 mmol). The resulting solution was heated at 85° C. for 24 h. The toluene was removed by rotary evaporation, MeOH (4 mL), THF (2 mL), and 20% NaOH (2 mL) were added, and the resulting mixture was refluxed for 24 h. THF and MeOH were removed by rotary evaporation, and the aqueous residue was adjusted to a pH of ~7 with 6M HCl. Extraction with ethyl acetate, drying, and concentration gave the crude acid which was further purified by column chromatography (10% and then 80% ethyl acetate in hexanes) to afford 583 mg (60% overall) of the acid 7a as a mixture of diastereoisomers. Crystallization from acetone/hexane afforded 204 mg (21% overall) of the pure major isomer: IR (KBr) 3300–2500, 1703, 1271, 1031 cm$^{-1}$; $^1$H NMR δ7.29 (d, 1H, J=8.5 Hz), 6.61 (d, 1H, J=8.5 Hz), 6.02 (m, 1H), 5.46 (m, 2H), 5.16 m, 2H), 3.93 (s, 3H), 3.50 (d, 1H, J=4.7 Hz), 2.97 (m, 2H), 2.70 (m, 1H), 2.16 (m, 2H), 1.75 (d, 3H) J=6.7 Hz), 1.55 (s, 3H); $^{13}$C NMR δ180.0, 162.7, 155.8, 137.9, 137.7, 134.5, 132.3, 128.8, 125.0, 117.0, 116.1, 108.7, 54.7, 53.3, 48.9, 45.4, 38.7, 35.6, 22.7, 13.6.

EXAMPLE 15

(11E)-Ethylidene-9,10-dihydro-2-methoxy-7,10-dimethyl-5,9-methanocycloocta[b]pyridine-5(6H)-carboxylic Acid (7b)

n-BuLi (1.75 mL, 2.8 mmol, 1.6M in hexane) was added dropwise to a mixture of ethyltriphenylphosphonium bromide (1.22 g, 3.29 mmol) in dry THF (10 mL) at rt under argon. The reaction mixture was stirred at rt for 1 h and then cooled to 0° C. The ketone 6b (210 mg, 0.7 mmol) in dry THF (5 mL) was added dropwise to this mixture at 0° C. The resulting mixture was allowed to warm to rt and stirred at rt for 2 h. The reaction mixture was quenched with water. THF was removed by rotary evaporation, and the aqueous residue was extracted with ethyl acetate. The extracts were washed with brine, dried, and concentrated. Flash chromatography (10% ethyl acetate in hexane) gave 198 mg of Z olefination product. A solution of this compound (198 mg, 0.63 mmol) and triflic acid (0.15 mL, 1.7 mmol) in dry dioxane (3.4 mL) was heated at 96° C. in a resealable robe under argon for 18 h. The dioxane was removed by rotary evaporation, and the residue was partitioned between aqueous $NaHCO_3$ and ethyl acetate. The organic layer was washed with brine, dried, and filtered. Concentration and flash chromatography (20% ethyl acetate in hexane) gave 178 mg of the isomerized intermediate. A solution of this olefin (178 mg, 0.57 mmol), AIBN (47 mg, 0.29 mmol), and PhSH (58 mL, 0.57 mmol) in dry toluene (6 mL) was heated at 85° C. for 1 day. The toluene was removed by rotary evaporation, MeOH (2 mL), THF (1 mL), and 20% NaOH (1 mL) were added, the resulting mixture was refluxed for 1 day. THF and MeOH were removed by rotary evaporation, and the aqueous residue was adjusted to a pH of ~7 with 6M HCl. Extraction with ethyl acetate, drying, and concentration gave the crude acid which was further purified by column chromatography (10% and then 80% ethyl acetate in hexanes) to afford 131 mg (63% overall) of the acid 7b as a mixture of diastereoisomers. Crystallization from acetone/hexane afforded 42 mg (20% overall) of the pure major isomer: IR (KBr) 3500–2500, 2924, 1703, 1475 cm$^{-1}$; $^1$H NMR δ11.5 (br s, 1H), 7.24 (d, 1H, J=8.6 Hz), 6.56 (d, 1H, J=8.6 Hz), 5.45 (m, 2H), 3.90 (s, 3H), 3.35 (d, 1H, J=4.6 Hz), 3.00 (m, 2H), 2.13 (d, 1H, J=17.0 Hz), 1.74 (d, 3H) J=6.7 Hz), 1.52 (s, 3H), 1.29 (d, 3H) J=7.2 Hz); $^{13}$C NMR δ 162.7, 157.4, 137.9, 134.6, 132.1, 126.5, 124.8, 116.5, 108.3, 54.7, 53.3, 45.0, 43.8, 39.1, 22.7, 20.2, 13.2; MS m/z 299 (M$^+$), 254, 118; HRMS calcd for $C_{18}H_{21}NO_3$ 299.1521, found 299.1504.

EXAMPLE 16

(11E)-10-Ethyl-11-ethylidene-9,10-dihydro-2-methoxy-7-methyl-5,9-methanocycloocta[b]pyridine-5(6H)-carboxylic Acid (7c) was prepared from 6c in the same manner as described for the preparation of compound 7b: IR (KBr) 3400–2500, 2945, 1701 cm$^{-1}$; $^1$H NMR δ7.22 (d, 1H, J=8.4 Hz), 6.54 (d, 1H, J=8.4 Hz), 5.41 (m, 2H), 3.89 (s, 3H), 3.50 (d, 1H, J=4.9 Hz), 2.98 (d, 1H, J=16.8 Hz), 2.68 (m, 1H), 2.12 (d, 1H, J=16.8 Hz), 1.85 (m, 1H), 1.73 (d, 3H, J=6.3 Hz), 1.51 (s, 3H), 1.48 (m, 1H), 1.12 (t, 3H) J=7.3 Hz); $^{13}$C NMR δ180.0, 162.6, 158.8, 137.6, 135.1, 132.2, 126.5, 125.1, 116.4, 108.3, 54.7, 53.3, 50.9, 45.4, 35.9, 27.4, 22.7, 13.3, 13.0.

EXAMPLE 17

(11E)-Ethylidene-9,10-dihydro-2-methoxy-7-methyl-10-propyl-5,9-methanocycloocta[b]pyridine-5(6H)-carboxylic Acid (7d) was prepared from 6d in the same manner as described for the preparation of compound 7b: IR (KBr) 3500–2500, 2957, 1705 cm$^{-1}$; $^1$H NMR δ7.23 (d, 1H, J=8.6 Hz), 6.54 (d, 1H, J=8.6 Hz), 5.41 (m, 2H), 3.89 (s, 3H), 3.47 (d, 1H, J=4.6 Hz), 2.98 (d, 1H, J=16.7 Hz), 2.82 (m, 1H), 2.12 (d, 1H, J=17 Hz), 1.72 (d, 3H), J=6.6 Hz), 1.54 (m, 4H), 1.52 (s, 3H), 0.97 (t, 3H, J=7.0 Hz); $^{13}$C NMR δ180.4, 162.5, 156.9, 137.7, 135.2, 132.2, 126.6, 125.0, 116.3, 108.2, 54.7, 53.3, 48.8, 45.4, 36.8, 36.4, 22.7, 21.4, 14.2, 13.2.

EXAMPLE 18

(11E)-10-Butyl-11-ethylidene-9,10-dihydro-2-methoxy-7-methyl-10-propyl-5,9-methanocycloocta[b]pyridine-5(6H)-carboxylic Acid (7e) was prepared from 6e in the same manner as described for the preparation of compound 7b: IR (KBr) 3500–2500, 2930, 1705, 1599, 1475 cm$^{-1}$; $^1$H NMR δ11.5 (br s, 1H), 7.24 (d, 1H, J=8.3 Hz), 6.55 (d, 1H, J=8.3 Hz), 5.44 (m, 2H), 3.90 (s, 3H), 3.48 (d, 1H, J=4.6 Hz), 3.00 (d, 1H, J=16.8 Hz), 2.80 (m, 1H), 2.13 (d, 1H, J=16.8 Hz), 1.80 (m, 1H), 1.74 (d, 3H) J=6.6 Hz), 1.52 (s, 3H), 1.49 (m, 5H), 0.93 (t, 3H) J=7.2 Hz); $^{13}$C NMR δ180.7, 162.5, 157.0, 137.7, 135.1, 132.2, 126.7, 125.0, 118.3, 108.1, 54.7, 53.3, 48.9, 45.3, 36.2, 34.2, 30.5, 22.7, 14.0, 13.3.

EXAMPLE 19

(11E)-10-Allyl-5-amino-11-ethylidene-5,6,9,10-tetrahydro-7-methyl-5,9-methanocycloocta[b]pyridin-5(1H)-one (8a).

A solution of the acid 7a (101 mg, 0.31 mmol), $NEt_3$ (43 mL, 0.31 mmol), and $(PhO)_2P(O)N_3$ (67 mL, 0.31 mmol) in dry toluene (8 mL) was heated at 85° C. for 3 h. After cooling, the solvent was removed by rotary evaporation, and the residue was dissolved in dry methanol (8 mL). The resulting mixture was refluxed for 24 h. After cooling and evaporation, the residue was directly purified by flash column chromatography (3% and then 10% ethyl acetate in methylene chloride) to give 77 mg of the urethane. To a solution of this urethane (77 mg, 0.22 mmol) in $CHCl_3$ (8 mL) was added TMSI (0.31 mL, 2.2 mmol) under argon at rt, and the reaction mixture was refluxed for 6 h. The residue was dissolved in dry MeOH (8 mL), and the resulting solution was refluxed under argon for 18 h. After cooling and evaporation, the residue was partitioned between aqueous $NaHCO_3$ and $CH_2Cl_2$. The organic layer was washed with brine, dried, and filtered. Concentration and flash chromatography on silica gel half-saturated with ammonia with 10% methanol in $CH_2Cl_2$ as eluent gave 55 mg (62% overall) of 8a: IR (KBr) 3423, 2924, 1656, 1618, 1465 cm$^{-1}$; $^1$H NMR δ7.88 (d, 1H, J=9.4 Hz), 6.41 (d, 1H, J=9.4 Hz), 6.00, 5.66 (q, 1H, J=6.7 Hz), 5.39 (d, 1H, J=4.3 Hz), 5.12 (m, 2H), 3.13 (d, 1H, J=4.9 Hz), 2.82 (m, 1H), 2.45 (m, 1H), 2.10 (m, 3H), 1.70 (d, 3H) J=6.7 Hz), 1.52 (s, 3H); $^{13}$C NMR δ165.1, 145.8, 140.3, 140.1, 136.6, 133.9, 124.7, 121.5, 117.8, 117.3, 113.4, 54.6, 49.7, 45.6, 38.3, 36.5, 22.5, 13.3.

EXAMPLE 20

(11E)-5-Amino-11-ethylidene-5,6,9,10-tetrahydro-7,10-dimethyl-5,9-methanocycloocta[b]pyridin-2(1H)-one (8b) was prepared from 7b in the same manner as described for the preparation of compound 8a: IR (KBr) 3422, 2924, 1655, 1601, 1458, 836 cm$^{-1}$; $^1$H NMR δ7.88 (d, 1H, J=9.4 Hz), 6.31(d, 1H, J=9.4 Hz), 5.65 (q, 1H, J=6.8 Hz), 5.44 (d, 1H, J=4.0 Hz), 3.30 (d, 1H, J=4.7 Hz), 2.95 (q, 1H, J=6.8 Hz), 2.09 (s, 2H), 1.70 (d, 3H) J=6.8 Hz), 1.53 (s, 3H), 1.27 (d, 3H, J=7 Hz); $^{13}$C NMR δ165.4, 147.5, 140.3, 133.6, 124.6, 121.3, 117.3, 113.1, 54.6, 49.4, 40.4, 40.0, 22.5, 20.0, 13.0; MS m/z 256 (M$^+$), 241, 227.

EXAMPLE 21

(11E)-5-Amino-10-ethyl-11-ethylidene-5,6,9,10-tetrahydro-7-methyl-5,9-methanocycloocta[b]pyridin-2(1H)-one (8c) was prepared from 7c in the same manner as described for the preparation of compound 8a: IR (KBr) 3422, 2924, 1655, 1601, 1458, 836 cm$^{-1}$; $^1$H NMR δ12.26 (br s, 1H), 7.85 (d, 1H, =9.4 Hz), 6.39 (d, 1H, J=9.4 Hz), 5.64 (q, 1H, J=6.7 Hz), 5.40 (d, 1H, J=3.9 Hz), 3.47 (d, 1H, J=4.7 Hz), 2.60 (d, 1H, J=8.3 Hz), 2.58 (s, 2H), 1.69 (d, 3H, J=6.7 Hz), 1.52 (s, 3H), 1.42 (m, 4H), 1.12 (t, 3H, J=7.3 Hz); $^{13}$C NMR δ165.0, 146.7, 40.8, 40.0, 133.6, 124.8, 121.2, 117.6, 113.1, 54.6, 49.6, 47.4, 36.3, 27.1, 22.6, 13.0, 12.8.

EXAMPLE 22

(11E)-5-Amino-11-ethylidene-5,6,9,10-tetrahydro-7-methyl-10-propyl-5,9-methanocycloocta[b]pyridin-2(1H)-one (8d) was prepared from 7d in the same manner as described for the preparation of compound 8a: IR (KBr) 3423, 2930, 1655, 1606, 1450 cm$^{-1}$; $^1$H NMR δ12.28 (br s, 1H), 7.84 (d, 1H, J=9.5 Hz), 6.37 (d, 1H, J=9.5 Hz), 5.64 (q, 1H, J=6.7 Hz), 5.40 (d, 1H, J=4.6 Hz), 3.44 (d, 1H, J=4.6 Hz), 2.69 (d, 1H, J=10.3 Hz), 2.07 (s, 2H), 1.68 (d, 3H, J=6.7 Hz), 1.52 (s, 3H), 1.50 (m, 6H), 0.93 (t, 3H, J=6.8 Hz); $^{13}$C NMR δ165.1, 146.9, 140.8, 140.0, 133.8, 124.8, 121.2, 117.5, 113.0, 54.8, 49.8, 45.7, 36.6, 36.2, 22.6, 21.4, 14.2, 12.9.

EXAMPLE 24

(11E)-5-Amino-10-butyl-11-ethylidene-5,6,9,10-tetrahydro-7-methyl-5,9-methanocycloocta[b]pyridin-2(1H)-one (8e) was prepared from 7e in the same manner as described for the preparation of compound 8a: IR (KBr) 3421, 2930, 1655, 1606, 1460 cm$^{-1}$; $^1$H NMR δ12.30 (br s, 1H), 7.84 (d, 1H, J=9.4 Hz), 6.37 (d, 1H, J=9.4 Hz), 5.63 (q, 1H, J=6.7 Hz), 5.39 (d, 1H, J=4.2 Hz), 3.45 (d, 1H, J=4.9 Hz), 2.67 (d, 1H, J=19.4 Hz), 2.07 (s, 2H), 1.68 (d, 3H, J=6.7 Hz), 1.51 (s, 3H), 1.42 (m, 8H), 0.89 (t, 3H) J=7.3 Hz); $^{13}$C NMR δ165.2, 147.0, 140.9, 140.0, 133.0, 124.9, 121.2, 117.5, 113.1, 54.6, 49.7, 46.0, 36.6, 33.9, 30.5, 22.9, 22.7, 14.1, 13.1.

All publications, patents and patent documents are incorporated by reference herein, as though fully set forth.

The invention has been described with reference to various specific and preferred embodiments and techniques. However, it should be understood that many variations and modifications may be made while remaining within the spirit and scope of the invention.

What is claimed is:

1. A compound of the formula:

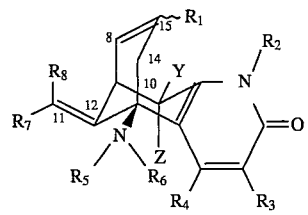

wherein one of Y and Z is H or (C$_1$–C$_8$)alkyl and the other of Y and Z is (C$_1$–C$_8$)alkyl, vinyl, (C$_3$–C$_8$)alkenyl, ethynyl or CH$_2$X wherein X is OH, F, OC(O)Ph, or OSO$_2$CF$_3$; or together Y and Z are carbonyl or methylene; R$_1$ is H, (C$_1$–C$_8$)alkyl, or halo; R$_2$ is H or (C$_1$–C$_8$)alkyl; R$_3$ and R$_4$ are individually H, (C$_1$–C$_8$)alkyl, NO$_2$, hydroxy, or halo; R$_5$ and R$_6$ are individually H, (C$_1$–C$_8$)alkyl, aryl, or aralkyl; R$_7$ is H, halo, or (C$_1$–C$_8$)alkyl, R$_8$ is halo or (C$_1$–C$_8$)alkyl; or a pharmaceutically acceptable salt thereof.

2. The compound of claim 1 wherein one of Y or Z is (C$_1$–C$_4$)alkyl or allyl.

3. The compound of claims 1 or 2 wherein Z is methyl.

4. The compound of claim 1 wherein R$_1$ is (C$_1$–C$_8$)alkyl.

5. The compound of claim 4 wherein R$_1$ is H, methyl or fluoro.

6. The compound of claim 5 wherein R$_7$ is H, and R$_8$ is (C$_1$–C$_8$)alkyl.

7. The compound of claim 6 wherein R$_3$ and R$_4$ are H.

8. The compound of claim 1 wherein R$_5$ and R$_6$ are H.

9. The compound of claim 1 wherein R$_3$ is (C$_1$–C$_4$)alkyl, NO$_2$, hydroxy or halo.

10. The compound of claim 1 wherein R$_4$ is (C$_1$–C$_4$)alkyl, NO$_2$, hydroxy or halo.

11. The compound of claims 9 or 10 wherein R$_4$ is chloro or methyl.

12. The compound of claim 1 wherein R$_8$ is halo.

13. A pharmaceutical composition comprising a therapeutically effective amount for the inhibition of the cholinesterase enzymes in a mammal of one or more compounds of claim 1 and a pharmaceutically acceptable carrier.

14. A therapeutic method comprising inhibiting the cholinesterase enzymes in a mammal by administering to said mammal an effective amount of one or more of the compounds of claim 1.

15. The compound of claim 12 wherein R$_8$ is chloro.

* * * * *

UNITED STATES PATENT AND TRADEMARK OFFICE
CERTIFICATE OF CORRECTION

PATENT NO. : 5,547,960

DATED : August 20, 1996

INVENTOR(S) : Alan P. Kozikowski et al.

It is certified that error appears in the above-identified patent and that said Letters Patent is hereby corrected as shown below:

In column 2, line 56 please delete "Of come" and insert --Of course--

In column 3, line 36 please delete " acetylcholinestemse ( ACHE) " should read insert -- acetylcholinesterase ( AChE ) --.

In column 3, line 46 please delete "ACHE" and insert --AChE--

In column 3, line 50 please delete "desipmmine" and insert --desipramine--

In column 5, line 28 please delete "2a" and insert --7a--

Signed and Sealed this

Fifth Day of August, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,547,960
DATED : August 20, 1996
INVENTOR(S) : Kozikowski et al.

Page 1 of 1

It is certified that error appears in the above-identified patent and that said Letters Patent is hereby corrected as shown below:

Column 1,
Line 4, insert

-- Statement of Government Rights

The invention was made at least in part with a grant from the Government of the United States of America (grant no. AG07591 from the National Institutes of Health). The Government has certain rights to the invention. --.

Signed and Sealed this

Twenty-first Day of May, 2002

Attest:

Attesting Officer

JAMES E. ROGAN
Director of the United States Patent and Trademark Office